(12) United States Patent
Boyan et al.

(10) Patent No.: US 8,202,701 B2
(45) Date of Patent: Jun. 19, 2012

(54) MICROENCAPSULATION OF CELLS IN HYDROGELS USING ELECTROSTATIC POTENTIALS

(75) Inventors: Barbara Dale Boyan, Atlanta, GA (US); Ramsey Christian Kinney, Atlanta, GA (US); Zvi Schwartz, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 1070 days.

(21) Appl. No.: 11/576,542

(22) PCT Filed: Oct. 7, 2005

(86) PCT No.: PCT/US2005/036202
§ 371 (c)(1),
(2), (4) Date: Jul. 19, 2007

(87) PCT Pub. No.: WO2006/042132
PCT Pub. Date: Apr. 20, 2006

(65) Prior Publication Data
US 2008/0031962 A1 Feb. 7, 2008

Related U.S. Application Data

(60) Provisional application No. 60/617,560, filed on Oct. 8, 2004.

(51) Int. Cl.
*C12Q 1/02* (2006.01)
(52) U.S. Cl. ........... 435/29; 435/174; 435/182; 435/382
(58) Field of Classification Search .................. 435/29, 435/174, 182, 382
See application file for complete search history.

(56) References Cited

U.S. PATENT DOCUMENTS

| | | | |
|---|---|---|---|
| 4,352,883 A | 10/1982 | Lim | |
| 4,391,909 A | 7/1983 | Lim | |
| 4,407,957 A | 10/1983 | Lim | |
| 4,663,286 A | 5/1987 | Tsang | 435/178 |
| 4,673,566 A | 6/1987 | Goosen | 424/19 |
| 4,744,933 A | 5/1988 | Rha | 264/4.3 |
| 4,789,550 A | 12/1988 | Hommel et al. | |
| 4,892,538 A | 1/1990 | Aebischer | 604/891.1 |
| 5,011,472 A | 4/1991 | Aebischer | 604/50 |
| 5,106,627 A | 4/1992 | Aebischer | 424/424 |
| 5,156,844 A | 10/1992 | Aebischer | 424/434 |
| 5,227,298 A | 7/1993 | Weber | 435/178 |
| 5,260,002 A | 11/1993 | Wang | 264/4.1 |
| 5,286,495 A | 2/1994 | Batich | 424/490 |
| 5,545,423 A | 8/1996 | Soon-Shiong et al. | 424/484 |
| 5,550,178 A | 8/1996 | Desai | 524/56 |
| 5,578,314 A | 11/1996 | Cochrum | 424/424 |
| 5,591,625 A | 1/1997 | Gerson | 435/240.2 |
| 5,620,883 A | 4/1997 | Shao | 435/174 |
| 5,648,099 A | 7/1997 | Batich | 424/497 |
| 5,656,468 A | 8/1997 | Dorian et al. | |
| 5,762,959 A | 6/1998 | Soon-Shiong et al. | 424/451 |
| 5,795,570 A | 8/1998 | Weber | 424/93.7 |
| 5,820,882 A | 10/1998 | Hubbell | 434/491 |
| 5,837,234 A | 11/1998 | Gentile | 424/93.7 |
| 5,876,742 A | 3/1999 | Cochrum et al. | |
| 5,888,814 A | 3/1999 | Kriegler | 435/360 |
| 5,916,790 A | 6/1999 | Enevold | 435/178 |
| 5,944,754 A | 8/1999 | Vacanti | 623/11 |
| 6,033,888 A | 3/2000 | Batich et al. | |
| 6,129,761 A | 10/2000 | Hubbell | 623/11 |
| 6,206,914 B1 | 3/2001 | Soykan | 623/1.42 |
| 6,242,230 B1 | 6/2001 | Batich | 435/178 |
| 6,383,478 B1 | 5/2002 | Prokop | 424/78.08 |
| 6,455,277 B1 | 9/2002 | Fox | 435/69.1 |
| 6,649,384 B2 | 11/2003 | Walsh | 435/178 |
| 6,656,508 B2 | 12/2003 | Goldenberg et al. | 424/484 |
| 6,660,301 B1 | 12/2003 | Vogel | 424/489 |
| 6,712,822 B2 | 3/2004 | Re | 606/86 |
| 6,713,293 B1 | 3/2004 | Grummt | 435/182 |
| 6,777,539 B2 | 8/2004 | Sprecher | 530/351 |
| 6,783,964 B2 | 8/2004 | Opara | 435/178 |
| 6,793,937 B2 | 9/2004 | Quong | 424/486 |
| 7,101,546 B2 | 9/2006 | Tsang | 424/93.7 |
| 7,138,251 B1 | 11/2006 | Fox et al. | 435/325 |
| 7,153,669 B2 | 12/2006 | Theill et al. | 435/69.1 |
| 7,189,695 B2 | 3/2007 | Sprecher | 530/351 |
| 7,282,222 B2 | 10/2007 | Phillips | 424/93.7 |
| 7,323,190 B2 | 1/2008 | Chu et al. | 424/426 |
| 7,338,657 B2 | 3/2008 | Vogel et al. | 424/93.7 |
| 7,371,576 B2 | 5/2008 | Tsang | 435/378 |
| 7,462,366 B2 | 12/2008 | Lanphere | 424/489 |
| 7,482,152 B2 | 1/2009 | Ramasubramanian | 435/283.1 |
| 7,527,971 B2 | 5/2009 | Musick | 435/325 |
| 7,547,547 B2 | 6/2009 | Dang et al. | 435/382 |

(Continued)

FOREIGN PATENT DOCUMENTS

CA 2437250 2/2005

(Continued)

OTHER PUBLICATIONS

Lim and Sun, "Microencapsulated islets as bioartificial endocrine pancreas", *Science*, 210(4472):908-10 (1980).

(Continued)

*Primary Examiner* — Allison Ford
*Assistant Examiner* — Susan E Fernandez
(74) *Attorney, Agent, or Firm* — Ballard Spahr LLP

(57) ABSTRACT

Compositions and methods for producing encapsulated cells having an average diameter of less than about 200 μm are provided. Methods for using the disclosed encapsulated cells are also provided.

14 Claims, 2 Drawing Sheets

U.S. PATENT DOCUMENTS

| | | | | |
|---|---|---|---|---|
| 7,576,186 | B2 | 8/2009 | Lum et al. | 530/387.3 |
| 7,629,452 | B2 | 12/2009 | Sprecher et al. | 536/23.5 |
| 7,727,555 | B2 | 6/2010 | Dicarlo | 424/489 |
| 7,790,699 | B2 | 9/2010 | Melvik et al. | 514/54 |
| 7,842,377 | B2 | 11/2010 | Lanphere et al. | 428/212 |
| 2003/0138948 | A1* | 7/2003 | Fisk et al. | 435/366 |
| 2003/0162284 | A1* | 8/2003 | Dordick et al. | 435/287.2 |
| 2004/0265386 | A1 | 12/2004 | Taylor | 424/489 |
| 2006/0159823 | A1 | 7/2006 | Melvik et al. | 514/54 |
| 2007/0048295 | A1 | 3/2007 | Chen | 424/451 |
| 2007/0116680 | A1 | 5/2007 | Stegeman | 435/325 |
| 2007/0178132 | A1 | 8/2007 | Giannetti et al. | 424/93.7 |
| 2008/0031858 | A1 | 2/2008 | Chan et al. | 424/93.7 |
| 2008/0118569 | A1 | 5/2008 | Vogel | 424/93.7 |
| 2008/0138416 | A1 | 6/2008 | Rauh et al. | 424/93.1 |
| 2009/0098177 | A1 | 4/2009 | Werkmeister et al. | 514/44 |
| 2009/0269313 | A1 | 10/2009 | Nadler | 424/93.7 |
| 2010/0055115 | A1 | 3/2010 | Lum | 424/133.1 |
| 2010/0136120 | A1 | 6/2010 | Marchosky | 424/422 |

FOREIGN PATENT DOCUMENTS

| | | |
|---|---|---|
| CA | 2561191 | 10/2005 |
| CN | 1962855 | 5/2007 |
| CN | 101508975 | 8/2009 |
| EP | 2174656 | 4/2010 |
| JP | 61-44823 | 3/1986 |
| JP | 2004-533500 | 11/2004 |
| WO | WO 02/30481 | 4/2002 |
| WO | WO 02/081662 A1 * | 10/2002 |
| WO | WO 03/080848 | 10/2003 |
| WO | WO 2005/097074 | 10/2005 |
| WO | WO 2010/062059 | 6/2010 |

OTHER PUBLICATIONS

Nigam, et al., "Techniques for preparing hydrogel membrane capsules", *Biotechnology Techniques*, 2(4):271-276 (1988).

Plunkett, et al., "An in vivo quantitative angiogenesis model using tumor cells entrapped in alginate", *Laboratory Investigation*, 62(4):510-517 (1990).

Smidsrod and Skjak-Braek, "Alginate as Immobilization Matrix for Cells", *Trends in Biotechnology*, 8(3):71-78 (1990).

Wolters, et al., "A versatile alginate droplet generator applicable for microencapsulation of pancreatic islets", *J. Appl. Biomater*, 3(4):281-6 (1991).

Bugarski, et al., "Methods for animal cell immobilization using electrostatic droplet generation," *Biotechnology Techniques*, 7(9):677-82 (1993).

Pjanovic, et al., "Immobilization/encapsulation of cells using electrostatic droplet generation," *Minerva Biotechnologica*, 12(4):241-8 (2000).

Strand, et al., "Alginate-polylysine-alginate microcapsules: effect of size reduction on capsule properties," *Journal of Microencapsulation*, 19(5):615-30 (2002).

U.S. Appl. No. 61/416,463, filed Nov. 23, 2010, Boyan et al.

U.S. Appl. No. 61/426,018, filed Dec. 22, 2010, Boyan et al.

Al Kindi AH, Asenjo JF, Ge Y, Chen GY, Bhathena J, Chiu RC, Prakash S, Shum-Tim D. (2011) Microencapsulation to reduce mechanical loss of microspheres: implications in myocardial cell therapy. Eur J Cardiothorac Surg. 39(2): 241-247.

Ashton RS, Banerjee A, Punyani S, Schaffer DV, Kane RS. (2007) Scaffolds based on degradable alginate hydrogels and poly(lactide-co-glycolide) microspheres for stem cell culture. Biomaterials. 28(36): 5518-5525.

Bhakta G, Lee KH, Magalhães R, Wen F, Gouk SS, Hutmacher DW, Kuleshova LL. (2009) Cryopreservation of alginate-fibrin beads involving bone marrow derived mesenchymal stromal cells by vitrification. Biomaterials. 30(3): 336-343.

Bhat A, Dreifke MB, Kandimalla Y, Gomez C, Ebraheim NA, Jayasuriya AC. (2010) Evaluation of cross-linked chitosan microparticles for bone regeneration. J Tissue Eng Regen Med. 4(7): 532-542.

Bidarra SJ, Barrias CC, Barbosa MA, Soares R, Granja PL. (2010) Immobilization of human mesenchymal stem cells within RGD-grafted alginate microspheres and assessment of their angiogenic potential. Biomacromolecules. 11(8): 1956-1964.

Bodenheimer T, Chen E, Bennett HD. (2009) Confronting the growing burden of chronic disease: can the U.S. health care workforce do the job? Health Aff (Millwood). 28(1): 64-74.

Bonaventure J, Kadhom N, Cohen-Solal L, Ng KH, Bourguignon J, Lasselin C, Freisinger P. (1994) Reexpression of cartilage-specific genes by dedifferentiated human articular chondrocytes cultured in alginate beads. Exp Cell Res. 212(1): 97-104.

Boontheekul T, Kong HJ, Mooney DJ. (2005) Controlling alginate gel degradation utilizing partial oxidation and bimodal molecular weight distribution. Biomaterials. 26(15): 2455-2465.

Bouhadir KH, Hausman DS, Mooney DJ. (1999) Synthesis of crosslinked poly(aldehyde guluronate) hydrogels. Polymer. 40: 3575-3584.

Bouhadir KH, Lee KY, Alsberg E, Damm KL, Anderson KW, Mooney DJ. (2001) Degradation of partially oxidized alginate and its potential application for tissue engineering. Biotechnol Prog. 17(5): 945-950.

Bugarski B, Smith J, Wu J, Goosen MFA. (1993) Methods for animal cell immobilizanon using electrostatic droplet generation. Biotechnology Techniques. 7(9): 677-682.

Constantinidis I, Rask I, Long RC Jr, Sambanis A. (1999) Effects of alginate composition on the metabolic, secretory, and growth characteristics of entrapped beta TC3 mouse insulinoma cells. Biomaterials. (21): 2019-2027.

Copland IB, Lord-Dufour S, Cuerquis J, Coutu DL, Annabi B, Wang E, Galipeau J. (2009) Improved autograft survival of mesenchymal stromal cells by plasminogen activator inhibitor 1 inhibition. Stem Cells. 27(2): 467-477.

Coutu DL, Cuerquis J, El Ayoubi R, Forner KA, Roy R, François M, Griffith M, Lillicrap D, Yousefi AM, Blostein MD, Galipeau J. (2011) Hierarchical scaffold design for mesenchymal stem cell-based gene therapy of hemophilia B. Biomaterials. 32(1): 295-305.

Da Costa A, Michaud P, Petit E, Heyraud A, Colin-Morel P, Courtois B, Courtois J. (2001) Purification and properties of a glucuronan lyase from Sinorhizobium meliloti M5N1CS (NCIMB 40472). Appl Environ Microbiol. 67(11): 5197-5203.

Endres M, Wenda N, Woehlecke H, Neumann K, Ringe J, Erggelet C, Lerche D, Kaps C. (2010) Microencapsulation and chondrogenic differentiation of human mesenchymal progenitor cells from subchondral bone marrow in Ca-alginate for cell injection. Acta Biomater. 6(2): 436-444.

Fonseca KB, Bidarra SJ, Oliveira MJ, Granja PL, Barrias CC. (2011) Molecularly designed alginate hydrogels susceptible to local proteolysis as three-dimensional cellular microenvironments. Acta Biomater. 7(4): 1674-1682.

Ghidoni I, Chlapanidas T, Bucco M, Crovato F, Marazzi M, Vigo D, Torre ML, Faustini M. (2008) Alginate cell encapsulation: new advances in reproduction and cartilage regenerative medicine. Cytotechnology. 58(1): 49-56.

Grellier M, Granja PL, Fricain JC, Bidarra SJ, Renard M, Bareille R, Bourget C, Amédée J, Barbosa MA. (2009) The effect of the co-immobilization of human osteoprogenitors and endothelial cells within alginate microspheres on mineralization in a bone defect. Biomaterials. 30(19): 3271-3278.

Gu F, Amsden B, Neufeld R. (2004) Sustained delivery of vascular endothelial growth factor with alginate beads. J Control Release. 96(3): 463-472.

Helmick CG, Felson DT, Lawrence RC, Gabriel S, Hirsch R, Kwoh CK, Liang MH, Kremers HM, Mayes MD, Merkel PA, Pillemer SR, Reveille JD, Stone JH; National Arthritis Data Workgroup. (2008) Estimates of the prevalence of arthritis and other rheumatic conditions in the United States. Part I. Arthritis Rheum. 58(1): 15-25.

Hernández RM, Orive G, Murua A, Pedraz JL. (2010) Microcapsules and microcarriers for in situ cell delivery. Adv Drug Deliv Rev. 62(7-8): 711-730.

Hwang YS, Cho J, Tay F, Heng JY, Ho R, Kazarian SG, Williams DR, Boccaccini AR, Polak JM, Mantalaris A. (2009) The use of murine embryonic stem cells, alginate encapsulation, and rotary microgravity bioreactor in bone tissue engineering. Biomaterials. 30(4): 499-507.

Jabbarzadeh E, Starnes T, Khan YM, Jiang T, Wirtel AJ, Deng M, Lv Q, Nair LS, Doty SB, Laurencin CT. (2008) Induction of angiogenesis in tissue-engineered scaffolds designed for bone repair: a combined gene therapy-cell transplantation approach. Proc Natl Acad Sci U S A. 105(32): 11099-11104.

Jayasuriya AC, Bhat A. (2009) Optimization of scaled-up chitosan microparticles for bone regeneration. Biomed Mater. 4(5): 055006, 8 Pages.

Kim BS, Kang KS, Kang SK. (2010) Soluble factors from ASCs effectively direct control of chondrogenic fate. Cell Prolif. 43(3): 249-261.

King A, Sandler S, Andersson A, Hellerström C, Kulseng B, Skjåk-Braek G. (1999) Glucose metabolism in vitro of cultured and transplanted mouse pancreatic islets microencapsulated by means of a high-voltage electrostatic field. Diabetes Care. 22 Suppl 2: B121-B126.

Klokk TI, Melvik JE. (2002) Controlling the size of alginate gel beads by use of a high electrostatic potential. J Microencapsul. 19(4): 415-424.

Koulinska I. (Nov. 2008) Cellular Therapies. Decision Resources: Waltham, Massachusetts, pp. 1-202.

Lawrence RC, Felson DT, Helmick CG, Arnold LM, Choi H, Deyo RA, Gabriel S, Hirsch R, Hochberg MC, Hunder GG, Jordan JM, Katz JN, Kremers HM, Wolfe F; National Arthritis Data Workgroup. (2008) Estimates of the prevalence of arthritis and other rheumatic conditions in the United States. Part II. Arthritis Rheum. 58(1): 26-35.

Lee CS, Moyer HR, Gittens RA, Williams JK, Boskey AL, Boyan BD, Schwartz Z. (2010) Regulating in vivo calcification of alginate microbeads. Biomaterials. 31(18): 4926-4934.

Lim F, Sun AM. (1980) Microencapsulated islets as bioartificial endocrine pancreas. Science. 210(4472): 908-910.

Lim JJ, Hammoudi TM, Bratt-Leal AM, Hamilton SK, Kepple KL, Bloodworth NC, McDevitt TC, Temenoff JS. (2011) Development of nano- and microscale chondroitin sulfate particles for controlled growth factor delivery. Acta Biomater. 7(3): 986-995.

Lin J, Lindsey ML, Zhu B, Agrawal CM, Bailey SR. (2007) Effects of surface-modified scaffolds on the growth and differentiation of mouse adipose-derived stromal cells. J Tissue Eng Regen Med. 1(3): 211-217.

Meliga E, Strem BM, Duckers HJ, Serruys PW. (2007) Adipose-derived cells. Cell Transplant. 16(9): 963-970.

Moioli EK, Hong L, Guardado J, Clark PA, Mao JJ. (2006) Sustained release of TGFbeta3 from PLGA microspheres and its effect on early osteogenic differentiation of human mesenchymal stem cells. Tissue Eng. 12(3): 537-546.

Moyer HR, Kinney RC, Singh KA, Williams JK, Schwartz Z, Boyan BD. (2010) Alginate microencapsulation technology for the percutaneous delivery of adipose-derived stem cells. Ann Plast Surg. 65(5): 497-503.

O'Brien M, Kaczor M. (2011) 2011 Orthopedic Outlook. William Blair & Company: Chicago, Illinois, pp. 1-46.

Oliveira SM, Almeida IF, Costa PC, Barrias CC, Ferreira MR, Bahia MF, Barbosa MA. (2010) Characterization of polymeric solutions as injectable vehicles for hydroxyapatite microspheres. AAPS PharmSciTech. 11(2): 852-858.

Orive G, De Castro M, Kong HJ, Hernández RM, Ponce S, Mooney DJ, Pedraz JL. (2009) Bioactive cell-hydrogel microcapsules for cell-based drug delivery. J Control Release. 135(3): 203-210.

Pierson RN 3rd, Dorling A, Ayares D, Rees MA, Seebach JD, Fishman JA, Hering BJ, Cooper DK. (2009) Current status of xenotransplantation and prospects for clinical application. Xenotransplantation. 16(5): 263-280.

Rada T, Reis RL, Gomes ME. (2009) Adipose tissue-derived stem cells and their application in bone and cartilage tissue engineering. Tissue Eng Part B Rev. 15(2): 113-125.

Raines AL, Olivares-Navarrete R, Wieland M, Cochran DL, Schwartz Z, Boyan BD. (2010) Regulation of angiogenesis during osseointegration by titanium surface microstructure and energy. Biomaterials. 31(18): 4909-4917.

Raines AL, Sunwoo M, Gertzman AA, Thacker K, Guldberg RE, Schwartz Z, Boyan BD. (2011) Hyaluronic acid stimulates neovascularization during the regeneration of bone marrow after ablation. J Biomed Mater Res A. 96(3): 575-583.

Rowley JA, Madlambayan G, Mooney DJ. (1999) Alginate hydrogels as synthetic extracellular matrix materials. Biomaterials. 20(1): 45-53.

Sadat S, Gehmert S, Song YH, Yen Y, Bai X, Gaiser S, Klein H, Alt E. (2007) The cardioprotective effect of mesenchymal stem cells is mediated by IGF-I and VEGF. Biochem Biophys Res Commun. 363(3): 674-679.

Sambanis A. (2003) Encapsulated islets in diabetes treatment. Diabetes Technol Ther. 5(4): 665-668.

Sawabe T, Ohtsuka M, Ezura Y. (1997) Novel alginate lyases from marine *Bacterium alteromonas* sp. strain H-4. Carbohydr Res. 304(1): 69-76.

Strand BL, Gåserød O, Kulseng B, Espevik T, Skjåk-Baek G. (2002) Alginate-polylysine-alginate microcapsules: effect of size reduction on capsule properties. J Microencapsul. 19(5): 615-630.

Tang SC, Sambanis A. (2004) Differential rAAV2 transduction efficiencies and insulin secretion profiles in pure and co-culture models of human enteroendocrine L-cells and enterocytes. J Gene Med. 6(9): 1003-1013.

Trouche E, Girod Fullana S, Mias C, Ceccaldi C, Tortosa F, Seguelas MH, Calise D, Parini A, Cussac D, Sallerin B. (2010) Evaluation of alginate microspheres for mesenchymal stem cell engraftment on solid organ. Cell Transplant. 19(12): 1623-1633.

Uludag H, De Vos P, Tresco PA. (2000) Technology of mammalian cell encapsulation. Adv Drug Deliv Rev. 42(1-2): 29-64.

Yu J, Du KT, Fang Q, Gu Y, Mihardja SS, Sievers RE, Wu JC, Lee RJ. (2010) The use of human mesenchymal stem cells encapsulated in RGD modified alginate microspheres in the repair of myocardial infarction in the rat. Biomaterials. 31(27): 7012-7020.

Zhao W, Zhang C, Jin C, Zhang Z, Kong D, Xu W, Xiu Y. (2010) Periurethral injection of autologous adipose-derived stem cells with controlled-release nerve growth factor for the treatment of stress urinary incontinence in a rat model. Eur Urol. 59(1): 155-163.

International Preliminary Report on Patentability issued Jul. 10, 2007 for PCT/US2005/036202 filed Oct. 7, 2005, (4 pages).

International Search Report issued Jun. 20, 2007 for PCT/US2005/036202, (3 pages).

Written Opinion issued Jun. 20, 2007 for PCT/US2005/036202 filed Oct. 7, 2005, (3 pages).

Communication pursuant to Article 94(3) EPC issued Sep. 12, 2011 for European Patent Application No. 05817171.1, (4 pages).

Claim Set filed Sep. 13, 2010 for European Patent Application No. 05817171.1, (5 pages).

Response to Article 94(3) EPC Communciation filed Sep. 6, 2010 for European Patent Application No. 05817171.1, (4 pages).

Cover Page for Communication pursuant to Article 94(3) EPC issued Feb. 23, 2010 for European Patent Application No. 05817171.1, (1 page).

Response to Rule 70(2) EPC Communication filed Jan. 13, 2010 for European Patent Application No. 05817171.1, (1 page).

Cover Page for Rule 70(2) EPC Communciation issued Nov. 16, 2009 for European Patent Applicatoin No. 05817171.1, (1 page).

Communciation conveying Extended Search Report issued Oct. 28, 2009 for European Patent Application No. 05817171.1, (8 pages).

Amended Claim Set filed Nov. 5, 2007 for European Patent Application No. 05817171.1, (5 pages).

Communication filed May 6, 2011 for Canadian Patent Application No. 2,583,308, (1 page).

Examiner's First Report issued Oct. 27, 2008 for Australian Patent Application No. 2005294200, (2 pages).

Office Action issued Jul. 26, 2011 for Japanese Application No. 2007-535844, (3 pages).

Amended Claim Set filed Oct. 6, 2008 for Japanese Application No. 2007-535844, (3 pages).

* cited by examiner

MICROENCAPSULATION OF CELLS IN HYDROGELS USING ELECTROSTATIC POTENTIALS

CROSS REFERENCE TO RELATED APPLICATION

The application is a 371 application of PCT/US2005/036202 filed Oct. 7, 2005, which claims priority to and benefit of U.S. Provisional Patent Application No. 60/617,560 filed on Oct. 8, 2004, and where permissible is incorporated by reference in its entirety.

STATEMENT REGARDING FEDERALLY SPONSORED RESEARCH OR DEVELOPMENT

Aspects of the work described herein were supported, in part, by Grant No. EEC-9731643 awarded by the National Science Foundation. Therefore, the US government has certain rights in the disclosed subject matter.

BACKGROUND

1. Technical Field

Aspects of the disclosed subject matter are broadly directed to methods and compositions for producing encapsulated cells and methods of using encapsulated cells, for example, in cellular arrays, screening protocols, and methods of treatment.

2. Related Art

High Throughput Screening (HTS) has been in use for at least the past ten years to screen large numbers of potential chemical compounds that may have pharmaceutical efficacy or which may be precursors to pharmaceuticals. A given investigation may involve the screening of on the order of about 10,000 compounds per day. The screening methods typically involve conducting a chemical reaction in the presence of a test compound to determine the effect of the test compound on the reaction. For example, compounds can be tested for the ability to inhibit or catalyze a desired chemical reaction or enzyme.

Cell based assays are also used in screening assays. With cell based assays, an aliquot of cells is contacted with a test compound to determine whether the test compound produces a desired or expected change in the cells. The test compound producing a change in the cells can be selected for further characterization. Cell based assays have certain advantages over simple chemical reaction assays. In particular, cell based assays can provide more detail on the physiological action of a test compound including, for example, uptake by cells or bioavailability. Unfortunately, cell based assays are not easily incorporated into HTS assays because it is difficult to standardize the number of cells contacted with various test compounds. Without standardizing the number of cells per reaction, meaningful comparisons between compounds are difficult to assess.

Small aliquots of cells having a uniform numbers of cells would facilitate automated manipulation of the cells during HTS. Additionally, such aliquots would be amendable to transplantation into a host using minimally invasive techniques.

Accordingly, there is a need for methods and compositions to produce aliquots of cells having predictable sizes and numbers of cells.

SUMMARY

Aspects of the present disclosure are generally directed to encapsulated cells, methods of producing encapsulated cells and uses thereof. One aspect provides a method for producing microencapsulated cells comprising applying an electrostatic potential to a droplet of cells suspended in a first solution comprising one or more types of monomers, wherein the electrostatic potential is in an amount sufficient to disrupt the surface tension of the droplet; and dropping the droplet into a polymerization solution from a distance sufficient to produce a structure encapsulating the cells with an average diameter of less than about 200 µm. The polymerization solution comprises a polymerizing agent that promotes the polymerization of the one or more types of monomers and optionally, a nutrient osmolyte, for example about 150 mM glucose.

Another aspect provides a cellular array comprising encapsulated cells produced according the present disclosure.

Still another aspect provides methods of treatment using the disclosed encapsulated cells. In particular aspects, the encapsulated cells are injected directly into pathology sites to repair damaged tissue or to secrete cytokines, growth factors, proteins, or combinations thereof. Because the average diameter of the disclosed encapsulate cells is less than about 200 µm, the encapsulated cells will be minimally damaged by shear forces produced during injection. Microcapsules having a diameter greater than 250 µm tend to block needles used to deliver the microcapsules to a host. Accordingly, the disclosed microcapsules having a diameter of less than about 250 µm, typically less than about 200 µm can be delivered to a host via injection with a standard surgical needle in an amount sufficient to treat the host.

DETAILED DESCRIPTION

Definitions

Figure 1:
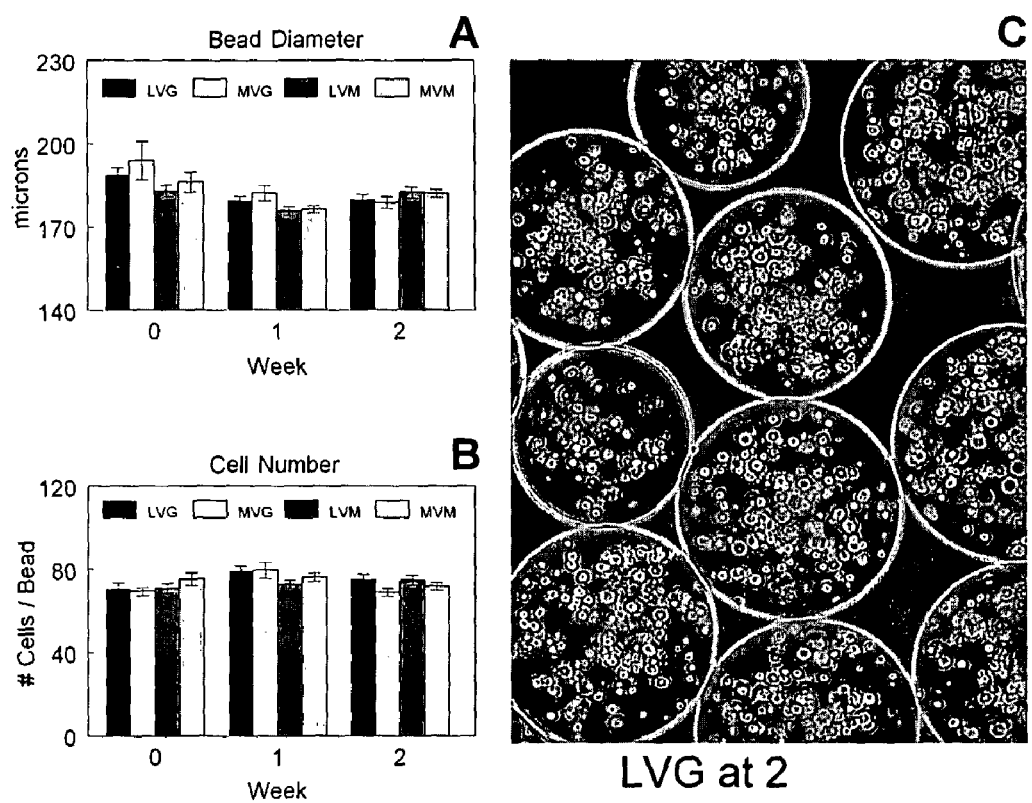
FIGS. 1A and 1B are bar graphs showing the average bead diameter of representative encapsulated cells to be 176±2 to 194±7 microns (A), and the average cell number per bead as 69±2 to 80±4 (B). There was no statistical difference in these parameters during the 2 week incubation time or between the different alginate formulations.
FIG. 1C shows a micrograph of representative beads and cells viewed by light microscopy.

In the present application, unless a contrary intention appears, the following terms refer to the indicated characteristics.

An "array", unless a contrary intention appears, includes any one-, two- or three-dimensional arrangement of addressable regions each having at least one unit of encapsulated cells optionally in combination with a particular chemical moiety or moieties (for example, biopolymers such as polynucleotide sequences) associated with that region. An array is "addressable" in that it has multiple regions of different moieties (for example, different cell types of chemicals) such that a region (a "feature" or "spot" of the array) at a particular predetermined location (an "address") on the array will detect a particular target or class of targets (although a feature may incidentally detect non-targets of that feature). Array features are typically, but need not be, separated by intervening spaces.

An "array layout" refers to one or more characteristics of the array or the features on it. Such characteristics include one or more of: feature positioning on the substrate; one or more feature dimension; some indication of an identity or function (for example, chemical or biological) of a moiety at a given location; how the array should be handled (for example, conditions under which the array is exposed to a sample, or array reading specifications or controls following sample exposure).

A "pulse jet" is a device which can dispense drops in the formation of an array. Pulse jets operate by delivering a pulse of pressure to liquid adjacent to an outlet or orifice such that a drop will be dispensed therefrom (for example, by a piezoelectric or thermoelectric element positioned in a same chamber as the orifice).

An array "package" my be the array plus only a substrate on which the array is deposited, although the package may include other features (such as a housing with a chamber).

A "chamber" references an enclosed volume (although a chamber may be accessible through one or more ports).

A "region" refers to any finite small area on the array that can be illuminated and any resulting fluorescence therefrom simultaneously (or shortly thereafter) detected, for example a pixel.

A "processor" references any hardware and/or software combination which will perform the functions required of it. For example, any processor herein may be a programmable digital microprocessor such as available in the form of a mainframe, server, or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic or optical disk may carry the programming, and can be read by a suitable disk reader communicating with each processor at its corresponding station.

It will also be appreciated that throughout the present application, that words such as "top", "upper", and "lower" are used in a relative sense only.

When one item is indicated as being "remote" from another, this is referenced that the two items are at least in different buildings, and may be at least one mile, ten miles, or at least one hundred miles apart. "Communication" information references transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data.

Reference to a singular item, includes the possibility that there are plural of the same items present.

"May" means optionally.

Methods recited herein may be carried out in any order of the recited events which is logically possible, as well as the recited order of events.

All patents and other references cited in this application, are incorporated into this application by reference where permissible except insofar as they may conflict with those of the present application (in which case the present application prevails).

Methods of Encapsulation

Embodiments of the disclosure are directed to methods and compositions for encapsulating cells and methods of using the encapsulated cells. Suitable cells include, but are not limited to differentiated mesenchymal cells, epithelial cells, neural cells, endothelial cells, epithelial cells, myoblasts, chondrocytes, myoblasts, osteoblasts, osteoclasts, bone marrow cells, adult stem cells, embryonic stem cells, umbilical cord blood cells, fibroblasts, or a combination thereof. Although the disclosure discusses the use of alginate as an exemplary encapsulation matrix, it will be appreciated by one of skill in the art that any polymeric may be used to encapsulate the cells provided that the monomers can be polymerized by the addition of a polymerizing agent. The polymerizing agent can be chemical, ionic, temperature, electromagnetic energy, or a combination thereof.

A first embodiment provides a method for producing microencapsulated cells by applying an electrostatic potential to a droplet of cells suspended in a first solution in an amount sufficient to disrupt the surface tension of the droplet. The first solution includes one or more types of monomers that will polymerize and encapsulate the cells. Exemplary polymeric materials suitable for encapsulating cells include, but are not limited to alginate, agarose, hyaluronic acid, collagen, synthetic monomers, albumin, fibrinogen, fibronectin, vitronectin, laminin, dextran, dextran sulfate, chondroitin sulfate, dermatan sulfate, keratin sulfate, chitin, chitosan, heparan, heparan sulfate, or a combination thereof. Polymerization is initiated by dropping the droplet into a polymerization solution from a distance sufficient to produce a structure encapsulating the cells having a predetermined average diameter. Generally, the average diameter of the structure formed during the encapsulation process is less than about 200 μm, less than about 150 μm, less than about 100 μm, or between about 150 to about 250 μm. The drop distance needed to produce microcapsules with a predetermined diameter and optionally, a predetermined number of cells can be determined using the general equations provided in Example 1. Suitable drop distances are from about 1 to about 10 cm, typically about 5 cm. Drop distance and electrostatic potential can be varied in combination to obtain encapsulated cells having a diameter of less than about 250 μM. One of skill in the art will recognize that the cell density of the first solution can be adjusted alone or in combination with the parameters shown in the equations in Example 1, in particular with the drop distance to obtain microcapsules having a predetermine diameter and cell number. Drop distance refers to the distance the droplet of cells falls before contacting the polymerization solution.

A representative encapsulation matrix includes, but is not limited to alginate. Generally, the use of alginate as an immobilization matrix for cells involves mixing a suspension of the cells with a sodium alginate solution, whereafter the mixture is dripped into a polymerization solution containing a polymerizing agent, for example multivalent cations (usually $Ca^{2+}$). The droplets form gel spheres instantaneously entrapping the cells in a three-dimensional lattice of ionically crosslinked alginate (Alginate as Immobilization Matrix for Cells" by Smidsrod and Skjak-Braek in Trends in Biotechnology, March 1990, Vol. 8, No. 3, pages 71-78). This immobilization procedure can be carried out under very mild conditions and is therefore compatible with most living cells. Generally, a 2% (w/v) solution of alginate in saline is sufficient for producing microcapsules having a diameter of less than about 200 μm, and less than about 100, 90, 80, or 70 total cells. The concentration of alginate con be varied to obtain a desired shape or size of encapsulated cells.

An exemplary polymerization solution comprises at least about 20 mM of a polymerizing agent such as $CaCl_2$. The amount of free $Ca^{2+}$ can be standardized using calcium ion chelators such as EGTA and/or EDTA. For example, a solution of EGTA can be titrated $CaCl_2$ to obtain a solution having a desired concentration of free calcium. Other polymerizing agents include, but are not limited to divalent cations and or chemical catalysts. Alternatively, the polymerization agent can be heat, light, or other form of thermal or electromagnetic energy.

The polymerization solution also may contain a nutrient osmolyte. The term "nutrient osmolyte" refers to a solute that is nutrient for the cells that helps maintain the osmotic balance of the solution to protect the cells fro swelling, bursting, or dehydrating. Glucose is a suitable nutrient osmolyte that may be used in the polymerization solution. The amount of glucose can be from about 50 to about 200 mM, typically about 150 mM.

A further embodiment provides a method of microencapsulating cells using alginate in combination with a second polymeric material, for example polyamino acids. Briefly, cells are suspended in sodium alginate in saline, and droplets containing cells are produced, for example by extruding the solution through a needle. An electrostatic potential is maintained between the droplets and the polymerization solution. Generally, about 6 kV is applied to obtain microcapsules having a diameter of less than about 200 μm.

Droplets of cell-containing alginate flow into calcium chloride in saline. The negatively charged alginate droplets bind calcium and form a calcium alginate gel. The microcapsules are washed in saline and incubated with a polyamino acid. Suitable polyamino acids include, but are not limited to poly-L-lysine, poly-L-ornithine, poly-L-arginine, poly-L-asparagine, poly-L-aspartic acid, poly-benzyl-L-aspartate, poly-S-benzyl-L-cysteine, poly-γ-benzyl-L-glutamate, poly-S-CBZ-L-cysteine, poly-ε-CBZ-D-lysine, poly-δCBZ-DL-ornithine, poly-O-CBZ-L-serine, poly-O-CBZ-D-tyrosine, poly(γ-ethyl-L-glutamate), poly-D-glutamic acid, polyglycine, poly-γ-N-hexyl L-glutamate, poly-L-histidine, poly(α, β-[N-(2-hydroxyethyl)-DL-aspartamide]), poly-L-hydroxyproline Poly(α,β-[N-(3-hydroxypropyl)-DL-aspartamide]), poly-L-isoleucine, poly-L-leucine, poly-D-lysine, poly-L-phenylalanine, poly-L-proline, poly-L-serine, poly-L-threonine, poly-DL-tryptophan, poly-D-tyrosine, or a combination thereof. In one embodiment, the positively charged poly-L-lysine and/or poly-L-ornithine displaces calcium ions and binds (ionic) negatively charged alginate, producing an outer poly-electrolyte membrane. A final coating of sodium alginate may be added by washing the microcapsules with a solution of sodium alginate, which ionically bonds to the poly-L-lysine and/or poly-L-ornithine layer. See U.S. Pat. No. 4,391,909 to Lim et al (all U.S. patents referenced herein are intended to be incorporated herein in their entirety). This technique produces what has been termed a "single-wall" microcapsule. Preferred microcapsules are essentially round, small, and uniform in size, for example having an average diameter of about 200 μm or less. Wolters et al., J. Appli Biomater. 3:281 (1992).

In a further embodiment, the alginate-polylysine microcapsules can then be incubated in a calcium chelator such as sodium citrate to solubilize any calcium alginate that has not reacted with poly-L-lysine, i.e., to solubilize the internal core of sodium alginate containing the cells, thus producing a microcapsule with a liquefied cell-containing core portion. See Lim and Sun, Science 210:908 (1980). Such microcapsules are referred to herein as having "chelated", "hollow" or "liquid" cores.

A "double-wall" microcapsule is produced by following the same procedure as for single-wall microcapsules, but prior to any incubation with sodium citrate, the microcapsules are again incubated with poly-l-lysine and sodium alginate.

A further embodiment provides microcapsules as described above having a final polymeric coating (e.g., polyethylene glycol (PEG)) or polyethylene oxide.

The encapsulating matrix may be formulated into a sponge-like material that is desirable for an implantable formulation. The matrices of the present invention may be formed into any shape by lyophilization or air drying in molds of the desired shape. Growth factors and/or therapeutic agents may be included in the matrix, and can include proteins originating from various animals including humans, microorganisms and plants, as well as those produced by chemical synthesis and using genetic engineering techniques. Such agents include, but are not limited to, biologically active substances such as growth factors such as, bFGF(FGF)-1), aFGF(FGF-2), EGF (epidermal growth factor), PDGF (platelet-derived growth factor), IGF (insulin-like growth factor), TGF-β1 through 3, including the TGF-β superfamily (BMPs, GDF-5, ADMP-1 and dpp); cytokines, such as various interferons, including interferon-alpha, -beta and -gamma, and interleukin-2 and -3; hormones, such as, insulin, growth hormone-releasing factor and calcitonin; non-peptide hormones; antibiotics; anti-cancer agents and chemical agents, such as, chemical mimetics of growth factors or growth factor receptors, and gene and DNA constructs, including cDNA constructs and genomic constructs.

In another embodiment, the agents include those factors, proteinaceous or otherwise, which are found to play a role in the induction or conduction of growth of bone, ligaments, cartilage or other tissues associated with bone or joints, such as for example, BMP and bFGF. One embodiment provides autologous or allogeneic cells encapsulated within the matrix. The autologous cells may be those naturally occurring in the donor or cells that have been recombinantly modified to contain one or more exogenous nucleic acids encoding desired protein products.

Alternative Polymeric Materials

The disclosed encapsulate cells can also contain water-soluble macromers, species, which are at once polymers and macromolecules capable of further polymerization. The macromers can be polymerized using a photoinitiator (such as a dye), optionally a cocatalyst, optionally an accelerator, or radiation in the form of visible or long wavelength UV light. The reaction occurs either by suspension polymerization or by interfacial polymerization. The polymer membrane can be formed directly on the surface of the biological material, or it can be formed on material which is already encapsulated.

Poly(ethylene oxide) (PEO) is an exemplary polymeric material that can be used with the disclosed encapsulated cells. The PEO chain is highly water soluble and highly flexible. Polymethylene glycol, on the other hand, undergoes rapid hydrolysis, while polypropylene oxide is insoluble in water. PEO chains have an extremely high motility in water and are completely non-ionic in structure. The synthesis and characterization of PEO derivatives which can be used for attachment of PEO to various surfaces, proteins, drugs etc. is known in the art. Other suitable polymers include poly(N-vinyl pyrrolidinone) and poly(ethyl oxazoline). These have been used to reduce interaction of cells with tissues. Water soluble ionic polymers, such as hyaluronic acid, can also be used to reduce cell adhesion to surfaces and can similarly be used.

Microcapsules

The methods of the present disclosure are intended for use with any microcapsule that contains living cells, for example cells secreting a desirable biological substance such as a hormone, protein, polysaccharide, or growth factor. One embodiment provides a microcapsule comprising an inner gel core containing the cells of interest, or a liquid core containing the cells of interest bounded by a semi-permeable membrane surrounding the cell-containing core. The inner core is preferably composed of a water-soluble gelling agent; preferably the water-soluble gelling agent comprises plural groups that can be ionized to form anionic or cationic groups. The presence of such groups in the gel allows the surface of the gel bead to be cross-linked to produce a membrane, when exposed to polymers containing multiple functionalities having a charge opposite to that of the gel.

Cells suspended in a gellable medium (such as alginate) may be formed into droplets using any suitable method as is known in the art, including but not limited to emulsification (see e.g., U.S. Pat. No. 4,352,883), extrusion from a needle (see, e.g., U.S. Pat. No. 4,407,957; Nigam et al., Biotechnology Techniques 2:271-276 (1988)), use of a spray nozzle (Plunkett et al., Laboratory Investigation 62:510-517 (1990)), or use of a needle and pulsed electrical electrostatic voltage (see, e.g., U.S. Pat. No. 4,789,550; U.S. Pat. No. 5,656,468).

The water-soluble gelling agent is preferably a polysaccharide gum, and more preferably a polyanionic polymer. An exemplary water-soluble gelling agent is an alkali metal alginate such as sodium alginate. The gelling agent preferably has free acid functional groups and the semi-permeable membrane is formed by contacting the gel with a polymer having free amino functional groups with cationic charge, to form crosslinks between the free amino acids of the polymer and the acid functional groups. Suitable polymers include poly-L-lysine, poly-L-ornithine, poly-L-arginine, poly-L-asparagine, poly-L-aspartic acid, poly-benzyl-L-aspartate, poly-S-benzyl-L-cysteine, poly-$\gamma$-benzyl-L-glutamate, poly-S-CBZ-L-cysteine, poly-$\epsilon$-CBZ-D-lysine, poly-$\delta$-CBZ-DL-ornithine, poly-O-CBZ-L-serine, poly-O-CBZ-D-tyrosine, poly($\gamma$-ethyl-L-glutamate), poly-D-glutamic acid, polyglycine, poly-$\gamma$-N-hexyl L-glutamate, poly-L-histidine, poly($\alpha$, $\beta$-[N-(2-hydroxyethyl)-DL-aspartamide]), poly-L-hydroxyproline Poly($\alpha$,$\beta$-[N-(3-hydroxypropyl)-DL-aspartamide]), poly-L-isoleucine, poly-L-leucine, poly-D-lysine, poly-L-phenylalanine, poly-L-proline, poly-L-serine, poly-L-threonine, poly-DL-tryptophan, poly-D-tyrosine, or a combination thereof.

A particularly preferred microcapsule contains cells immobilized in a core of alginate optionally with a second polymeric coating, for example a poly-lysine coating; such microcapsules may comprise an additional external alginate layer to form a multi-layer to form a multi-layer alginate-polylysine-alginate microcapsule. See U.S. Pat. No. 4,391,909 to Lim et al, the contents of which are incorporated by reference herein in their entirety.

When desired, the microcapsules may be treated or incubated with a physiologically acceptable salt such as sodium sulfate or like agents, in order to increase the durability of the microcapsule, while retaining or not unduly damaging the physiological responsiveness of the cells contained in the microcapsules. By "physiologically acceptable salt" is meant a salt that is not unduly deleterious to the physiological responsiveness of the cells encapsulated in the microcapsules. In general, such salts are salts that have an anion that binds calcium ions sufficiently to stabilize the capsule, without substantially damaging the function and/or viability of the cells contained therein. Sulfate salts, such as sodium sulfate and potassium sulfate, are preferred, and sodium sulfate is most preferred. The incubation step is carried out in an aqueous solution containing the physiological salt in an amount effective to stabilize the capsules, without substantially damaging the function and/or viability of the cells contained therein as described above. In general, the salt is included in an amount of from about 0.1 or 1 millimolar up to about 20 to 100 millimolar, most preferably about 2 to 10 millimolar. The duration of the incubation can be from about 1 to 10 minutes to about 1 or 2 hours, or more (e.g., over night). The temperature at which the incubation step is carried out is typically from about 4 degrees Celsius up to about 37 degrees Celsius, with room temperature (about 21 degrees Celsius) preferred.

When desired, liquefaction of the alginate gel may be carried out by any suitable method as is known in the art, such as ion exchange or chelation of calcium ion by chelators including, but not limited to sodium citrate, ethylene glycol bis (beta-aminoethylether)-N,N'tetraacetic acid (EGTA) or ethylenediaminetetraacetic acid (EDTA).

One embodiment provides microcapsules comprising a cell-containing core and optionally one or more layers surrounding the cell-containing core that permit the diffusion of nutrients, biologically active molecules and other selected products through the surface membrane and into the microcapsule core and can be used to limit the exchange of substances by size or charge. For example, the surface membrane can contain pores of a size that determines the molecular weight cut-off of the membrane. Where the microcapsule contains protein-secreting cells, the membrane pore size is chosen to allow the passage of the protien from the core to the external environment, but to exclude the entry of host immune response factors.

Arrays

A further embodiment provides an array comprising units of encapsulated cells deposited at addressable locations of a substrate. For example, each addressable location may contain one or more units of encapsulated cells or one or more test compounds. The unit of encapsulated cells can be a single bead of alginate encapsulated cells having an average diameter of less than about 200 $\mu$m and containing a predetermined number of cells. Each unit may contain approximately the same number of cells, typically plus or minus 40, 30, 20, or 10 or less cells. The encapsulated cells may be attached to the array substrate using any conventionally means, for example, polysaccharides, polyamino acids, or a combination thereof.

In an embodiment, the present method can include reacting multiple cellular arrays with standard mixtures or additions of test compounds. The method can then include comparing the amount of signal detected at each corresponding location or feature on two or more of the arrays. Standardizing the arrays can be based on this comparison.

In an embodiment, the present method can include detecting a first detectable signal (e.g., color) from the disclosed arrays and a second detectable signal from a standard mixture of the control compounds. The method can include comparing the strength of the first and second detectable signals. Quantitating the signal generated by the test compounds with control compounds can be based on this comparison.

Contacting can include any of a variety of known methods for contacting an array with a reagent, sample, or composition. For example, the method can include placing the array in a container and submersing the array in or covering the array with the reagent, sample, or composition. The method can include placing the array in a container and pouring, pipetting, or otherwise dispensing the reagent, sample, or composition onto features on the array. Alternatively, the method can include dispensing the reagent, sample, or composition onto features of the array, with the array being in or on any suitable rack, surface, or the like.

Detecting can include any of a variety of known methods for detecting a detectable signal from a feature or location of an array. Any of a variety of known, commercially available apparatus designed for detecting signals of or from an array can be employed in the present method. Such an apparatus or method can detect one or more of the detectable labels described herein below. For example, known and commercially available apparatus can detect colorimetric, fluorescent, or like detectable signals of an array. The methods and systems for detecting a signal from a feature or location of any array can be employed for monitoring or scanning the array for any detectable signal. Monitoring or detecting can include viewing (e.g., visual inspection) of the array by a person.

The disclosed arrays or compositions can be provided in any variety of common formats. The present encapsulated cells can be provided in a container, for example, as a liquid. In an embodiment, each of a plurality of disclosed encapsulated cells and arrays is provided in its own container (e.g., vial, tube, or well). The present disclosed encapsulated cells and arrays or compositions can be provided with materials for creating a cellular array or with a complete cellular array. In fact, the encapsulated cells can be provided bound to one or more features of a cellular array.

Arrays on a substrate can be designed for testing against any type of sample, whether a trial sample, reference sample, a combination of them, or a known mixture of test compounds. Any given substrate may carry one, two, four or more arrays disposed on a front surface of the substrate. Depending upon the use, any or all of the arrays may be the same or different from one another and each may contain multiple spots or features. A typical array may contain more than ten, more than one hundred, more than one thousand more ten thousand features, or even more than one hundred thousand features, in an area of less than 50 cm$^2$, 20 cm$^2$, or even less than 10 cm$^2$, or less than 1 cm$^2$. For example, features may have widths (that is, diameter, for a round spot) in the range from a 10 µm to 1.0 cm. In other embodiments each feature may have a width in the range of 1.0 µm to 1.0 mm, of 5.0 µm to 500 µm, or of 10 µm to 200 µm. Non-round features may have area ranges equivalent to that of circular features with the foregoing width (diameter) ranges. Feature sizes can be adjusted as desired, for example by using one or a desired number of pulses from a pulse jet to provide the desired final spot size.

Substrates of the arrays can be any solid support, a colloid, gel or suspension. Exemplary solid supports include, but are not limited to metal, metal alloys, glass, natural polymers, non-natural polymers, plastic, elastomers, thermoplastics, pins, beads, fibers, membranes, or combinations thereof.

At least some, or all, of the features are of different compositions (for example, when any repeats of each feature composition are excluded the remaining features may account for at least 5%, 10%, or 20% of the total number of features), each feature typically being of a homogeneous composition within the feature. Thus, certain feature may contain one type of cell encapsulated as described and a second feature may contain a second type of cell encapsulated as described. Interfeature areas will typically (but not essentially) be present which do not carry any polynucleotide (or other biopolymer or chemical moiety of a type of which the features are composed). Such interfeature areas typically will be present where the arrays are formed by processes involving drop deposition of reagents by may not be present when, for example, photolithographic array fabrication processes are used. It will be appreciated though, that the interfeature areas, when present, could be of various sizes and configurations.

Array features will generally be arranged in a regular pattern (for example, rows and columns). However other arrangements of the features can be used when the user has, or is provided with, some means (for example, through an array identifier on the array substrate) or being able to ascertain at least information on the array layout (for example, any one or more of feature composition, location, size, performance characteristics in terms of significance in variations of binding patterns with different samples, or the like). Each array feature is generally of a homogeneous composition.

Each array may cover an area of less than 100 cm$^2$, or even less than 50 cm$^2$, 10 cm$^2$, or 1 cm$^2$. In many embodiments, the substrate carrying the one or more arrays will be shaped generally as a rectangular solid (although other shapes are possible), having a length of more than 4 mm and less than 1 m, for example, more than 4 mm and less than 600 mm, less than 400 mm, or less than 100 mm; a width of more than 4 mm and less than 1 m, for example, less than 500 mm, less than 400 mm, less than 100 mm, or 50 mm; and a thickness of more than 0.01 mm and less than 5.0 mm, for example, more than 0.1 mm and less than 2 mm, or more than 0.2 and less than 1 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, the substrate may transmit at least 20%, or 50% (or even at least 70%, 90%, or 95%), of the illuminating light incident on the front as may be measured across the entire integrated spectrum of such illuminating light or alternatively at 532 nm or 633 nm.

Arrays can be fabricated using drop deposition from pulse jets of either test compound solutions or units of encapsulated cells. Other drop deposition methods can also be used for fabrication.

One embodiment provides a method of spotting a uniform number of mammalian cells at a plurality of locations of a substrate comprising applying an electrostatic potential to a succession of droplets of cells suspended in a first solution comprising one or more types of monomers, wherein the electrostatic potential is in an amount sufficient to disrupt the surface tension of each successive droplet. Each droplet is then dropped into a polymerization solution from a distance sufficient to produce a structure encapsulating a predetermined number of cells, wherein each structure produced comprises the predetermined number of cells plus or minus forty or less cells. The encapsulated cells are positioned at an addressable location of the substrate.

Methods Employing Arrays

Following receipt by a user of an array made according to the present disclosure, it will typically be exposed to a sample (for example, a test compound) in any well known manner and the array is then read. Reading of the array may be accomplished by illuminating the array and reading the location and intensity of resulting fluorescence at multiple regions on each feature of the array. Arrays may be read by any method or apparatus known in the art, with other reading methods including other optical techniques (for example, detecting chemiluminescent or electroluminescent labels) or electrical techniques (where each feature is provided with an electrode to detect hydridization at the feature). Data from read arrays may be processed in any known manner, such as from commercially available array feature extraction software packages. A result obtained from the reading followed by a method of the present invention may be used in that form or may be further processed to generate a result such as that obtained by forming conclusions based on the pattern read from the array (such as whether or not a particular target sequence may have been present in the sample, or whether or not a pattern indicates a particular condition of an organism from which the sample came). A result of the reading (whether further processed or not) may be forwarded (such as by communication) to a remote location if desired, and received there for further use (such as further processing).

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

Detectable Labels

The disclosed encapsulated cells and arrays can include a detectable label, for example, a first detectable label. A second detectable label can be generated when the test compound contacts encapsulated cells on an array. Suitable labels include radioactive labels and non-radioactive labels, directly detectable and indirectly detectable labels, and the like. Directly detectable labels provide a directly detectable signal without interaction with one or more additional chemical agents. Suitable of directly detectable labels include colorimetric labels, fluorescent labels, and the like. Indirectly detectable labels interact with one or more additional members to provide a detectable signal. Suitable indirect labels include a ligand for a labeled antibody and the like.

Suitable fluorescent labels include: xanthene dyes, e.g., fluorescein and rhodamine dyes, such as fluorescein isothiocyanate (FITC), 6-carboxyfluorescein (commonly known by the abbreviations FAM and F), 6-carboxy-2',4',7',4,7-hexachlorofluorescein (HEX), 6-carboxy-4',5'-dichloro-2',7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine-6G (RG6G5 or G5), 6-carboxyrhodamine-6G (R6G6 or G6), and rhodamine 110; Alexa dyes, e.g., Alexa-fluor-547; cyanine dyes, e.g., Cy3, Cy5 and Cy7 dyes; coumarins, e.g., umbelliferone; benzimide dyes, e.g., Hoechst 33258; phenanthridine dyes, e.g., Texas Red; ethidium dyes; acridine dyes; carbazole dyes; phenoxazine dyes; porphyrin dyes; polymethine dyes, e.g., cyanine dyes such as Cy3, Cy5, etc; BODIPY dyes and quinoline dyes.

Cryopreservation of Cells

Methods of cryopreservation are well known in the art. In general terms, cryopreservation of animal cells involves freezing the cells in a mixture of a growth medium and another liquid that prevents water from forming ice crystals, and then storing the cells at liquid nitrogen temperatures (e.g., from about −80 to about −196° C.).

One embodiment provides the cryopreservation of isolated and encapsulated mammalian cells in a cryopreservation medium. Another embodiment provides cryopreservation of isolated cells followed by microencapsulation of the cells prior to in vivo implantation.

Screening Methods

One of the several embodiments of the disclosure provides methods for identifying lead compounds, for example, using a combinatorial library of chemical compounds. Certain embodiments provide methods for identifying modulators of a target protein or cell function. As used herein the terms "test compound" refers to any molecule that may potentially inhibit or enhance the biological activity of a target protein, physiological pathway, or cellular function. The test compound can be a protein or fragment thereof, a small molecule, or even a nucleic acid molecule. The disclosure contemplates using lead compounds to help develop improved compounds which includes not only comparisons with known inhibitors and activators of a target protein or cell function, but predictions relating to the structure of target molecules.

One embodiment provides a method for identifying lead compounds using a high through put assay to contact units of encapsulated cells comprising a predetermined and optionally standardized number of cells and selecting the test compound that promotes or causes a change in phenotype of the encapsulated cells compared to a control compound. The change in phenotype includes, but is not limited to, morphological changes, color changes, changes in DNA or protein synthesis, changes in transcription or gene expression, changes in secretion, or a combination thereof.

In another embodiment, small molecule libraries that are believed to meet the basic criteria for useful drugs can be screened to identify useful compounds. Screening of such libraries, including combinatorially generated libraries (e.g., expression libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Test compounds may include fragments or parts of naturally-occurring compounds, or may be found as active combinations of known compounds, which are otherwise inactive. Compounds isolated from natural sources, such as animals, bacteria, fungi, plant sources, including leaves and bark, and marine samples can be assayed as candidates for the presence of potentially useful pharmaceutical agents. It will be understood that the pharmaceutical agents to be screened could also be derived or synthesized from chemical compositions or man-made compounds. Thus, it is understood that the test compound identified by embodiments of the present disclosure may be peptide, polypeptide, polynucleotide, small molecule inhibitors, small molecule inducers, organic or inorganic, or any other compounds that may be designed based on known inhibitors or stimulators.

Other suitable test compounds include antisense molecules, catalytic nucleic acids such as ribozymes, and antibodies (including single chain antibodies), each of which would be specific for a target protein or cellular function of interest.

In addition to the compounds initially identified, other sterically similar compounds may be formulated to mimic the key portions of the structure of the test compounds, for example binding domains. Such compounds, which may include peptidomimetics of peptide modulators, may be used in the same manner as the initial test compounds.

An inhibitor or activator according to the present disclosure may be one which exerts its inhibitory or activating effect upstream, downstream, directly, or indirectly on a target protein or cellular function. In one embodiment, the inhibition or activation or a target protein by an identified test compound results a detectable phenotypic change of the encapsulated cells compared to that observed in the absence of the added test compound.

Assay endpoints may be assayed using standard methods such as FACS, FACE, ELISA, Northern blotting and/or Western blotting. Moreover, the assays can be conducted using genetically engineered cells, immortalized cells, cell lines, primary cell cultures, autologous cells, or a combination thereof.

Various cell lines can be utilized for such screening assays, including cells specifically engineered for this purpose. Suitable cells include, but are not limited to differentiated mesenchymal cells, epithelial cells, neural cells, endothelial cells, epithelial cells, myoblasts, chondrocytes, myoblasts, osteoblasts, osteoclasts, bone marrow cells, adult stem cells, embryonic stem cells, umbilical cord blood cells, fibroblasts, or a combination thereof. Cells can also be engineered to express or overexpress compounds or proteins in response to contact with a test compound. Furthermore, those of skill in the art will appreciate that stable or transient transfections, which are well known and used in the art, may be used in the disclosed embodiments.

For example, a transgenic cell comprising an expression vector can be generated by introducing the expression vector into the cell. The introduction of DNA into a cell or a host cell is well known technology in the filed of molecular biology and is described, for example, in Sambrook et al., Molecular Cloning $3^{rd}$ Ed. (2001). Methods of transfection of cells include calcium phosphate precipitation, liposome mediated transfection, DEAE dextran mediated transfection, electroporation, ballistic bombardment, and the like. Alternatively, cells may be simply transfected with an expression vector using conventional technology described in the references and examples provided herein. The host cell can be a prokaryotic or eukaryotic cell, or any transformable organism that is capable of replicating a vector and/or expressing a heterologous gene encoded by the vector. Numerous cell lines and cultures are available for use as a host cell, and they can be obtained through the American Type Culture Collection (ATCC), which is an organization that serves as an archive for living cultures and genetic materials (www.atcc.org).

A host cell can be selected depending on the nature of the transfection vector and the purpose of the transfection. A plasmid or cosmid, for example, can be introduced into a prokaryote host cell for replication of many vectors. Bacterial cells used as host cells for vector replication and/or expression include DH5α, JM109, KC8, as well as a number of commercially available bacterial hosts such as SURE® Competent Cells and SOLOPACK™ Gold Cells (STRATAGENE, La Jolla, Calif.). Alternatively, bacterial cells such as *E. coli* LE392 could be used as host cells for phage viruses. Eukaryotic cells that can be used as host cells include, but are not limited to, yeast, insects and mammals. Examples of mammalian eukaryotic host cells for replication and/or expression of a vector include, but are not limited to, HeLa, NIH3T3, Jurkat, 293, Cos, CHO, Saos, and PC12. Examples of yeast strains include, but are not limited to, YPH499, YPH500 and YPH501. Many host cells from various cell types and organisms are available and would be known to one of skill in the art. Similarly, a viral vector may be used in conjunction with either an eukaryotic or prokaryotic host cell, particularly one that is permissive for replication or expression of the vector.

Depending on the assay, culture may be required. The cell is examined using any of a number of different physiologic assays. Alternatively, molecular analysis may be performed, for example, looking at protein expression, mRNA expression (including differential display of whole cell of polyA RNA) and others.

Methods of Treatment

Transplantation

Encapsulated cells produced according to the present disclosure may be transplanted into subjects as a treatment of pathologies including, but not limited to tissue damage, ischemia, insulin-dependent diabetes, heart attack, nerve damage, brain damage, bone damage, or cartilage repair. Such transplantation may be into the peritoneal cavity of the subject, or directly into a pathology site. Preferably, the encapsulated cells are injected directly into the site as needed. Because the average diameter of the encapsulate cells is less than about 200 μm, the encapsulated cells will be minimally damaged by shear forces produced during injection. Microcapsules having a diameter greater than 250 μm tend to block needles used to deliver the microcapsules to a host. Accordingly, the disclosed microcapsules having a diameter of less than about 250 μm, typically less than about 200 μm can be delivered to a host via injection with a standard surgical needle, for example a 14 gauge or 18 gauge needle, in an amount sufficient to treat the host.

The encapsulated cells can be genetically engineered to secrete a polypeptide needed to treat the pathology, for example insulin to control glycemia. It will be apparent to those skilled in the art that the quantity of microcapsules transplanted depends on the ability of the microcapsules to provide function in vivo. One skilled in the art will be able to determine suitable transplantation quantities of microcapsules, using techniques as are known in the art.

A further embodiment provides a method for treating a host comprising delivering encapsulated cells to host produced according to the present disclosure. For example, the encapsulated cells can produce cartilage or cartilage components in the host.

A further embodiment provides a method for repairing tissue in a host comprising administering encapsulated cells produced according the present disclosure, wherein the encapsulated cells produce tissue or tissue components in the host.

The following examples are provided for purposes of illustration and are not intended to limit the invention in any way.

EXAMPLES

Example 1

Encapsulation of Cells

Ultrapure alginate compositions containing polysaccharides with ≧60% guluronate or mannuronate resides with average molecular weights > or <200,000 g/mole were used. Each alginate powder was sterilized using UV light and dissolved in 0.9% saline to produce a 2% (w/v) alginate solution. Rat chondrocytes suspended in a minimum volume of saline were added to the alginate solution resulting in $6 \times 10^6$ cells/ml. The solution was then extruded through a 0.18 mm (inner diameter) needle at 10 ml/hr. A 6,000 kV electrostatic potential between the $CaCl_2$ polymerization solution and the needle was used to disrupt the surface tension. Bead size and total cell number per bead were determined by morphometric analysis.

Cell number and bead size were controlled by varying the distance the cell suspension dropped before hitting the polymerization solution. Additional parameters were modulated according to the following generalized equations to obtain encapsulated cells having a diameter of less than 200 μm and containing a predetermined number of cells.

$$P_i - P_o = \frac{2\gamma}{R}$$

$$P_o = \frac{F_s}{A}$$

$$A = 4\pi R^2$$

$$\frac{F_s}{4\pi R^2} - P_o = \frac{2\gamma}{R}$$

$$F_s = 4\pi R^2 \left( \frac{2\gamma}{R} + P_o \right)$$

$P_i$=pressure inside droplet $P_o$=pressure outside droplet (atmospheric pressure)
γ=surface tension of cell suspension
A=surface area of droplet
R=radius of droplet
$F_s$=surface force on droplet $$F_e = -qE$$

$$E = \frac{V}{d}$$

$$F_e = -\frac{qV}{d}$$

$F_e$=electrostatic force
V=applied voltage
d=distance from needle to solution
q=charge on droplet
E=electric field $$F_e > F_s$$

$$-\frac{qV}{d} > 4\pi R^2\left(\frac{2\gamma}{R} + P_o\right)$$

$$(4\pi P_o)R^2 + (8\pi\gamma)R + \frac{qV}{d} < 0$$

$4\pi P_o$ = pressure term $8\pi\gamma$ = surface tension term $\frac{qV}{d}$ = electrostatic term

Example 2

Effect of Alginate Composition on Microencapsulation

Alginate is co-polysaccharide composed of guluronate and mannuronate residues. The residue ratio and length of the polymer chains affect the mechanical properties of the alginate hydrogel. Four different alginate formulations (Table 2) were compared based on bead morphometrics and cell viability during two weeks of in vitro culture.

TABLE 1

Optimization of Microencapsulation Process

| Gelation Solution | Alginate Concentration | Bead Morphology | Cell Viability |
|---|---|---|---|
| 100 mM $CaCl_2$ | 2.0% | Spherical | <50% |
| 50 mM $CaCl_2$ + 75 mM NaCl | 2.0% | Irregular | ~50% |
| 20 mM $CaCl_2$ + 120 mM NaCl | 2.0% | Irregular | ~70% |
| 50 mM $CaCl_2$ + 150 mM Glucose | 2.0% | Spherical | ~90% |

TABLE 2

Alginate Compositions

| | Guluronate Content | |
|---|---|---|
| Molecular Weight | >60% | <40% |
| <200,000 g/mole | LVG | LVM |
| >200,000 g/mole | MVG | MVM |

The average bead diameter was 176±2 μm to 194±7 μm depending on the alginate composition used (FIG. 1A), but there was not statistically significant difference. In addition, no significant change in bead diameter was measured during the two weeks of in vitro culture. The initial cell number per bead was 69±2 to 75±3 (FIG. 1B), which corresponded to the loading density of $6 \times 10^6$ cells/ml. No significant change in cell number was observed over two weeks in any of the alginate compositions. The beads and encapsulated cells were easily viewed by light microscopy and remained intact and uniform during the two weeks of culture (FIG. 1C).

Example 3

Viability of Encapsulated Cells

Figure 2:
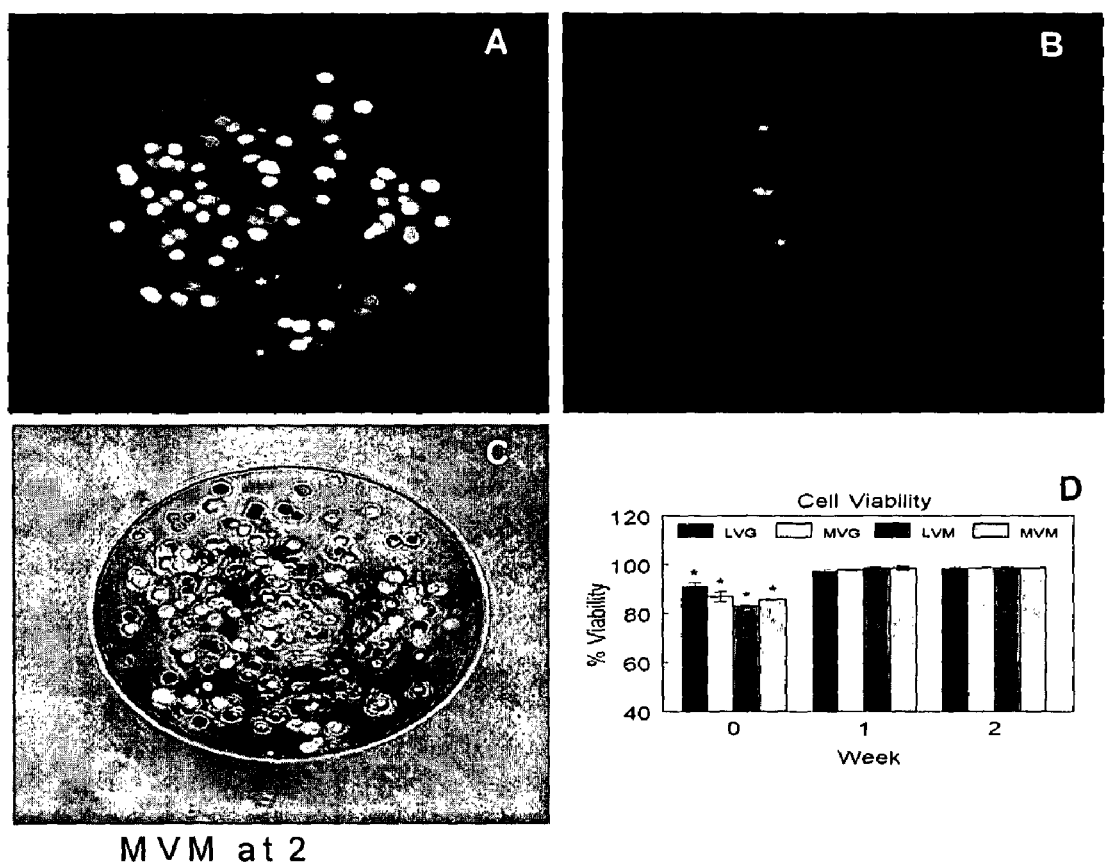
FIGS. 2A-C show fluorescent confocal micrograph of exemplary encapsulated cells using a calcein/ethidium homodimer-1 stain (A-C). The initial viability was 83% to 91%.
FIG. 2D shows a bar graph indicating viability increased after 1 week to >98% for all alginate compositions. *P<0.05, Initial vs. End Point.

The viability of the encapsulated chondrocytes was measured by fluorescent confocal microscopy and a live/dead stain consisting of calcein and ethidium homodimer-1. The calcein stains the cytoplasm of the live cells green (FIG. 2A) and the ethidium stains the nucleus of dead cells red (FIG. 2B). The live cells were evenly distributed throughout the beads (FIG. 2C) with an initial viability if 83% to 91% (FIG. 2D). The viability increased after one week in culture to greater than 98% for all alginate compositions and remained constant up to two weeks. No statistically significant differences were observed between the different alginate compositions on cell viability during the in vitro culture.

Example 4

In Vivo Implantation of Encapsulated Cells

The effects of alginate composition on encapsulated chondrocytes implanted in the hind gastroenemius muscles of athymic mice for 4 weeks was investigated. The legs were harvested and stained with hematoxylin and eosin. Histological analysis did not show any obvious cartilaginous tissue, but the cells within the beads appeared to be alive at the time of harvest and had a round morphology characteristic of normal chondrocytes. In addition, the beads were surrounded by a dense cellularity with a basophilic matrix. It was unclear if the cellularity was infiltrating host tissue or donor cells migrating out of the implanted beads. The cellularity did not appear to be inflammatory and there was minimal fibrosis.

We claim:
1. A method for selecting a compound comprising:
   (a) contacting encapsulated cells with at least one test compound, wherein the encapsulated cells are spotted on addressable locations on a substrate and the cells are encapsulated in a structure having a diameter of less than about 200 μm; and
   (b) selecting the compound that induces or promotes a change in phenotype of the encapsulated cells contacted with the test compound compared to a control, wherein the encapsulated cells are produced by a process comprising applying an electrostatic potential to a droplet of cells suspended in a first solution comprising one or more types of monomers, wherein the electrostatic potential is in an amount sufficient to disrupt the surface tension of the droplet, and dropping the droplet into a polymerization solution from a distance sufficient to produce a structure encapsulating from about 60 to about 100 cells with a diameter of less than about 200 μm, wherein the polymerization solution comprises a nutrient osmolyte and an ionic polymerizing agent that promotes the polymerization of the one or more types of monomers.

2. The method of claim 1, wherein the encapsulated cells comprise mammalian cells.

3. The method of claim 2, wherein the mammalian cells comprise differentiated mesenchymal cells, epithelial cells, neural cells, endothelial cells, epithelial cells, myoblasts, chondrocytes, myoblasts, osteoblasts, osteoclasts, bone marrow cells, adult stem cells, embryonic stem cells, umbilical cord blood cells, fibroblasts, or a combination thereof.

4. The method of claim 1, wherein the encapsulated cells comprise at least one exogenous nucleic acid.

5. The method of claim 1, wherein the cells are encapsulated in a polysaccharide polymer.

6. The method of claim 5, wherein the polymer comprises alginate, agarose, polyaminoacids, or a combination thereof.

7. The method of claim 1, wherein the phenotype change comprises a change in protein synthesis, DNA synthesis, gene expression, color, morphology, size, cell number, cell viability, secretion, or a combination thereof.

8. The method of claim 1, wherein the process of producing the encapsulated cells further comprises the step of treating the encapsulated cells with a second polymeric material comprising polyamino acids.

9. The method of claim 8, wherein the polyamino acids are selected from the group consisting of poly-L-lysine, poly-L-ornithine, poly-L-arginine, poly-L-asparagine, poly-L-aspartic acid, poly-benzyl-L-aspartate, poly-S-benzyl-L-cysteine, poly-γ-benzyl-L-glutamate, poly-S-CBZ-L-cysteine, poly-ε-CBZ-D-lysine, poly-δ-CBZ-DL-ornithine, poly-O-CBZ-L-serine, poly-O-CBZ-D-tyrosine, poly(γ-ethyl-L-glutamate), poly-D-glutamic acid, polyglycine, poly-γ-N-hexyl L-glutamate, poly-L-histidine, poly(α,β-[N-(2-hydroxyethyl)-DL-aspartamide]), poly-L-hydroxyproline, poly(α,β-[N-(3-hydroxypropyl)-DL-aspartamide]), poly-L-isoleucine, poly-L-leucine, poly-D-lysine, poly-L-phenylalanine, poly-L-proline, poly-L-serine, poly-L-threonine, poly-DL-tryptophan, poly-D-tyrosine, and a combination thereof.

10. The method of claim 1, wherein the ionic polymerizing agent comprises a divalent cation.

11. The method of claim 10, wherein the divalent cation is a calcium cation.

12. The method of claim 1, wherein the droplet of cells comprises about 60 to about 100 cells suspended in a solution of alginate.

13. The method of claim 1, wherein the polymerization solution comprises at least 20 mM $CaCl_2$.

14. The method of claim 1, wherein the nutrient osmolyte comprises glucose.

* * * * *